United States Patent [19]

Yamamoto et al.

[11] Patent Number: 5,512,484
[45] Date of Patent: Apr. 30, 1996

[54] CARROT 16 KD PROTEIN, GENE CODING FOR SAID PROTEIN AND PLASMID CONTAINING SAID GENE

[75] Inventors: Mika Yamamoto, Sakado; Kenji Oheda, Kyoto, both of Japan

[73] Assignee: Sumitomo Chemical Company, Limited, Osaka, Japan

[21] Appl. No.: 363,010

[22] Filed: Dec. 23, 1994

[30] Foreign Application Priority Data

Dec. 24, 1993 [JP] Japan .................................. 5-327943

[51] Int. Cl.$^6$ .......................... C12N 15/63; C07H 21/04; C07K 14/415
[52] U.S. Cl. ...................... 435/320.1; 536/23.6; 530/379
[58] Field of Search ................ 536/23.6; 435/320.1; 530/379

[56] References Cited

U.S. PATENT DOCUMENTS 5,451,516  5/1995  Matthews et al. ...................... 435/190

FOREIGN PATENT DOCUMENTS 06598842A  6/1995  European Pat. Off. .

OTHER PUBLICATIONS

Bryant, J. D. et al. (1992) "Isolation and partial characterization of alpha–and beta–carotene–containing carotenoprotein from carrot (*Daucus carota* L.) root chromoplasts" *J. Agri. Food Chem.* 40(4):545–549.

Kurosaki, F. et al. (1991) "6–Hydroxymellein synthetase as a multifunctional enzyme complex in elicitor–treated carrot root extract" *FEBS Lett.* 288(1,2):219–221.

Moorhead, G. B. G. et al. (1990) "Purification and characterization of cytosolic aldolase from carrot storage root" *Biochem. J.* 269:133–139.

Turano, F. J. et al. (1992) "Identification and expression of a cDNA clone encoding aspartate aminotransferase in carrot" *Plant Physiol.* 100:374–381.

*Primary Examiner*—Robert A. Wax
*Assistant Examiner*—Kawai Lau
*Attorney, Agent, or Firm*—Birch, Stewart, Kolasch & Birch

[57] ABSTRACT

There are disclosed a protein corresponding to a molecular weight of approximately 16 kD, which can be specifically expressed in carrot roots, a gene coding for the protein, and a plasmid containing the gene.

4 Claims, 6 Drawing Sheets

```
carrot 16kD protein       MGAQSHSLEITSSVSAEKIFSGIVLDVDTVIPKAAPGAYKSVD-VKGDGGAGTVRIITLP
parsley PR protein 1-3    MGVQKSEVEATSSVSAEKLFKGLCLDIDTLLPRVLPGAIKSSETLEGDGGVGTVKLVHLG
parsley PR protein 1-1    MGVQKSEVETTSSVSAEKLFKGLCLDIDTLLPQVLPGAIKSSETLEGDGGVGTVKLVHLG
                          ** *     * ******** * *     *    *      ** *   * carrot 16kD protein       EGSPITSMTVRTDAVNKEALTYDSTVIDGDILLEFIESIETHMVVVPTADGGSITKTTAI
parsley PR protein 1-3    DASPFKTMKQKVDAIDKATFTYSYSIIDGDILLGFIESINNHFTAVPNADGGCTVKSTII
parsley PR protein 1-1    DASPFKTMKQKVDAIDKATFTYSYSIIDGDILLGFIESINNHFTAVPNADGGCTVKSTII
                          . **  *  **  *   . *** *** *    **    * * * carrot 16kD protein       FHTKGDAVVPEENIKFADAQNTALFKAIEAYLIAN
parsley PR protein 1-3    FNTKGDAVVPEENIKFANDQNLTIFKAVEAYLIAN
parsley PR protein 1-1    FNTKGDAVVPEENIKFANDQNLTIFKAVEAYLIAN
                          * ************** **   *** *******
```

N-terminus 1                                                                          35
GAQSHSLEITSSVSAEKIFSGIVLDVDTVIPKAAP

FIG. 2

```
carrot 16kD protein      MGAQSHSLEITSSVSAEKIFSGIVLDVDTVIPKAAPGAYKSVD-VKGDGGAGTVRIITLP
parsley PR protein 1-3   MGVQKSEVEATSSVSAEKLFKGLCLDIDTLLPRVLPGAIKSSETLEGDGGVGTVKLVHLG
parsley PR protein 1-1   MGVQKSEVETTSSVSAEKLFKGLCLDIDTLLPQVLPGAIKSSETLEGDGGVGTVKLVHLG
                         ** . * ****** * .. . * ** ..* carrot 16kD protein      EGSPITSMTVRTDAVNKEALTYDSTVIDGDILLEFIESIETHMVVPTADGGSITKTTAI
parsley PR protein 1-3   DASPFKTMKQKVDAIDKATFTYSYSIIDGDILLGFIESINNHFTAVPNADGGCTVKSTII
parsley PR protein 1-1   DASPFKTMKQKVDAIDKATFTYSYSIIDGDILLGFIESINNHFTAVPNADGGCTVKSTII
                         :*.* .** . .**..:* ** ******** ****** **  ****  * ****.

carrot 16kD protein      FHTKGDAVVPEENIKFADAQNTALFKAIEAYLIAN
parsley PR protein 1-3   FNTKGDAVVPEENIKFANDQNLTIFKAVEAYLIAN
parsley PR protein 1-1   FNTKGDAVVPEENIKFANDQNLTIFKAVEAYLIAN
                         *.***************.  ** *:***.******
```

CARROT 16 KD PROTEIN, GENE CODING FOR SAID PROTEIN AND PLASMID CONTAINING SAID GENE

FIELD OF THE INVENTION

The present invention relates to a carrot 16 kD protein, and more particularly, it relates to a protein corresponding to a molecular weight of approximately 16 kD, which can specifically expressed in carrot roots. The present invention further relates to a gene coding for said protein and a plasmid containing said gene.

BACKGROUND OF THE INVENTION

It is well known that reserve proteins are present in the subterranean storage tissue of sweet potatoes, white potatoes and the like. By contrast, the presence of reserve proteins has not yet been found in the subterranean tissue of root vegetables which are crops having edible roots, such as carrots.

Carrot roots have been used as a root vegetable for food; it has, however, been found that they contain only small amounts of proteins essential to the maintenance of health. Thus, it has been desired that high-protein carrots are developed by higher expression of proteins which are present in small amounts but specifically in the carrot roots. For this purpose, it has been necessary to find, first of all, proteins which can be specifically expressed in carrot roots and genes coding for these proteins.

SUMMARY OF THE INVENTION

Under these circumstances, the present inventors have intensively studied. As a result, they have found a soluble protein which can be specifically expressed in carrot roots, and succeeded in the cloning of cDNA coding for said protein. Further, they have determined the amino acid sequence of said protein by analyzing the base sequence of said cDNA, thereby completing the present invention.

Thus, the present invention provides: a protein corresponding to a molecular weight of approximately 16 kD, which can be specifically expressed in carrot roots, and having the amino acid sequence as shown in Sequence Listing, SEQ ID NO: 1; a gene containing a coding region for the amino acid sequence of said protein, SEQ. I.D. NO.: 2; and a plasmid containing said gene.

BRIEF DESCRIPTION OF THE DRAWINGS

FIG. 2 shows the N-terminal amino acid sequence (one-character representation) of the protein of the present invention. This sequence corresponds to the amino acids from the 2nd to the 36th positions in the amino acid sequence as shown in Sequence Listing, SEQ ID NO: 1.

FIG. 6 shows the results of the search on the data bases EMBL and NBRF to examine the homology of the protein of the present invention.

DETAILED DESCRIPTION OF THE INVENTION

Figure 1:
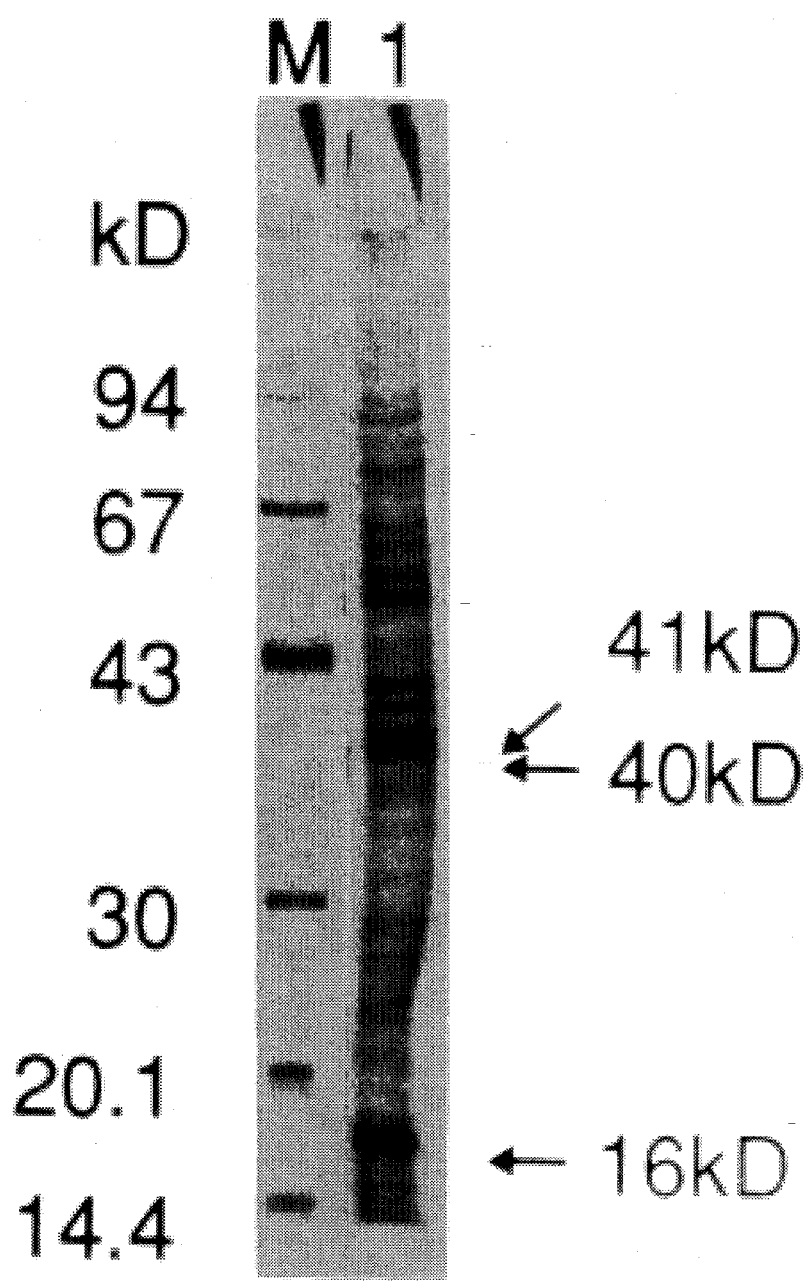
FIG. 1 shows the results of the SDS-polyacrylamide electrophoresis (with silver staining) which was performed with all the proteins present in carrot roots as a sample. Lane M is corresponding to a molecular weight marker; and lane 1, the sample. The arrow indicates the band corresponding to the protein of the present invention.

As used herein, the term "gene" refers to all the corresponding nucleic acids with genetic information, including genomic DNAs, their corresponding mRNAs and their corresponding cDNAs. The gene of the present invention is to be construed to include genes each containing a coding region for the amino acid sequence as shown in Sequence Listing, SEQ ID NO: 1, but each corresponding to another base sequence than the base sequence as shown Sequence Listing, SEQ ID NO: 2.

The protein of the present invention can be widely found in many varieties of carrots (*Daucus carota* L.), such as "Kuroda Gosun", "Early Chantenee", "Imperator" and "Nuntesscarlet", and it is specifically present in their roots. The protein of the present invention has a molecular weight of approximately 16 kD (the calculated value based on the amino acid sequence is 16,125.03). The protein of the present invention has the amino acid sequence as shown in Sequence Listing, SEQ ID NO: 1, which is further corresponding to, for example, the base sequence as shown in Sequence Listing, SEQ ID NO: 2. The utilization of a gene coding for the amino acid sequence of such a protein of the present invention makes it possible to develop high-protein carrots, and the introduction and expression of said gene into other root vegetable crops such as radishes, turnips, sugar beets and burdocks make it possible to perform the breeding of these crops for increasing the amount of proteins. Further, the search on data bases such as EMBL and NBRF for genes and amino acid sequences, which have a high degree of homology with the base sequence coding for the protein of the present invention and the corresponding amino acid sequence, respectively, makes it possible to attain, for examples, the following matters: (1) when they have a high degree of homology with the gene and amino acid sequence of a certain protein related to disease resistance, the breeding for imparting a resistance to disease and the elucidation of a mechanism of the disease resistance can be attained by ordinary techniques for genetic engineering using the gene containing a coding region for the amino acid sequence of the protein of the present invention; (2) when they have a high degree of homology with the gene and amino acid sequence of a certain protein expressed and derived in response to the change of various plant hormones, various kinds of breeding which make use of stress response or hormone response can be attained by ordinary techniques for genetic engineering using the gene containing a coding region for the amino acid sequence of the protein of the present invention; (3) when they have a high degree of homology with the gene and amino acid sequence of a certain protein responsible for pollen allergy, the breeding of non-allergic varieties with an improvement of pollen and a reduction in the amount of pollen expressed can be attained by ordinary techniques for genetic engineering using the gene containing a coding region for the amino acid sequence of the protein of the present invention; and (4) when they have a high degree of homology with the gene and amino acid sequence of a certain heat-shock protein, the improvement in the storage of useful proteins thorough the support of their holding and the effective utilization for the breeding to improve the transport of useful proteins can be attained by ordinary techniques for genetic engineering using the gene containing a coding region for the amino acid sequence of the protein of the present invention.

The protein of the present invention is present in the root tissues of many varieties of commercially available carrots, such as "Kuroda Gosun", "Early Chantenee", "Imperator" and "Nuntesscaret", and it is one of the soluble proteins which can be extracted from these root tissues.

For the separation, purification or detection of the protein of the present invention, for example, the following method can be used.

First of all, root tissues are thoroughly ground with an ordinary buffer used for soluble-protein extraction, such as a solution of potassium phosphate or sodium borate, by a commercially available mixer or a whirling blender, and the tissue residue is removed by filtration with gauze or by centrifugation at 10,000 rpm for about 10 minutes to give a crude extract of the protein of the present invention. The above buffer for soluble-protein extraction may optionally contain a reducing agent such as ascorbic acid or 2-mercaptoethanol.

The amount of the buffer for soluble-protein extraction to be used for the extraction of the protein of the present invention from the root tissues can be, for example, about 10 ml to about 100 ml, preferably about 10 ml to about 25 ml, per 5 g of the root tissues.

The above crude extract of the protein of the present invention can be suitably concentrated by ultrafiltration with Centriprep-10 (Amicon) or the like.

For the separation and purification of the protein of the present invention from the above crude extract on the basis of a difference in molecular weight, there can be used an ordinary method such as SDS-polyacrylamide gel electrophoresis (U.K. Laemrrdi, Nature, 227, 680 (1970)) or liquid chromatography through gel filtration. The use of such a method results in that the protein of the present invention is separated to have a size of approximately 16 kD in molecular weight. Further, the protein of the present invention can be simply detected by an immunological method using a polyclonal or monoclonal antibody which is prepared by using, as an antigen, a fraction separated and purified by liquid chromatography through gel filtration or a fraction cut out after the separation in a gel by SDS-polyacrylamide gel electrophoresis.

The gene of the present invention can be obtained according to an ordinary method for genetic engineering as described in, for example, J. Sambrook, E. F. Frisch, & T. Maniatis, *Molecular Cloning*, 2nd ed., Cold Spring Harbor Laboratory, 1989.

This method will hereinafter be explained in detail. First of all, the entire RNA is extracted by an ordinary method such as guanidine hydrochloride/phenol method, SDS-phenol method or guanidine thiocyanate/CsCl method, in which the plant tissues of various plants are ground in a solution containing a strong protein-denaturing agent such as guanidine hydrochloride or guanidine thiocyanate, and proteins and other contaminants are removed by centrifugation or by phenol or chloroform extraction, after which the entire RNA is collected by ethanol precipitation. As a kit based on these methods, for example, ISOGEN (Nippon Gene) and Extraction-A-PLANT™ RNA ISOLATION KIT (Clontech) are commercially available. For the purification of only mRNA from the entire RNA obtained, affinity chromatography utilizing hybridization between the poly-A tail of the mRNA and the oligo-dT tract combined with cellulose is effective. Oligo-dT cellulose is commercially available from Pharmacia or Collaborative. The poly-A tail-containing mRNA extracted from the column is collected by ethanol precipitation. As a method for the synthesis of cDNA from this poly-A tail-containing mRNA, there can be mentioned, for example, ordinary methods in which (1) the mRNA is used as a template and an oligo-dT primer is annealed to the poly-A tail thereof, after which first-strand DNA is synthesized by reverse transcriptase, followed by insertion of nicks and gaps in the RNA sequence using *Escherichia coli* RNaseH; the fragments of the RNA are then used as the subsequent primers to synthesize double-strand DNA using *E. coli* DNA polymerase I; (2) further, both ends are made blunt by T4 DNA polymerase, after which the resulting cDNA is purified and collected by phenol or chloroform extraction or by ethanol precipitation (as described in U. Gubler & B. J. Hoffman, *Gene*, 25, 263 (1983); H. Okayama & P. Berg, *Mol. Cell. Biol.*, 2, 161 (1982)). As a kit based on these methods, for example, cDNA synthesis system PLUS (Amersham) is commercially available.

The cDNA thus obtained is ligated to an appropriate linker and an appropriate adaptor at both blunt ends using T4 DNA ligase, and excess free linkers and adapters are separated by gel filtration or the like, followed by ligation to an appropriate vector arm such as a λ phage-derived vector. Further, phage particles formed by in vitro packaging are inoculated into *E. coli* cells to form a plaque on the medium. In this manner, a cDNA library can be prepared.

For the selection of cDNA clones containing a coding region for the amino acid sequence of the protein of the present invention from the cDNA library, for example, immunoscreening with an antibody against the protein of the present invention is effective in a vector system such as λgt 11, or plaque hybridization in which an oligonucleotide having the base sequence presumed from the amino acid sequence of the protein of the present invention is synthesized and labelled with a radioactive isotope (RI) or fluorescent reagent to use as a probe is effective in a vector system such as λgt 10. Further, screening can also be effected by purifying DNA of the cDNA-containing phage and then conducting southern blot hybridization using the DNA as a probe.

The above probe can be produced by an ordinary method in which the number and sequence of amino acids at the N-tern-final side are determined by the analysis of the purified protein of the present invention with an amino acid sequencer based on the Edman degradation (e.g., Amino Acid Sequencer 473A, Applied Biosynthesis), and the information on the amino acid sequence is used for substitution with a series of base codons presumed therefrom.

The cDNA clone thus obtained, which contains a coding region for the amino acid sequence of the protein of the present invention, is subcloned into a plasmid vector favorable for DNA preparation and analysis (e.g., commercially available pUC18) to prepare plasmid DNA, from which the cDNA base sequence of the protein of the present invention can be determined by the Maxam Gilbert method (see A. M. Maxam & W. Gilbert, *Proc. Natl. Acad. Sci.*, 74, 560 (1977)) or the Sanger method (see F. Sanger & A. R. Coulson, *J. Mol. Biol.*, 94, 441 (1975); and F. Sanger, S. Nicklen & A. R. Coulson, *Proc. Natl. Acad. Sci.*, 74, 5463 (1977)).

To determine the base sequence of genomic DNA from the cDNA of the protein of the present invention, for example, plant tissues such as those of leaves, stems and roots are instantaneously frozen with liquid nitrogen, and thoroughly ground with a mortar and pestle or with a whirling blender. From the ground material obtained, genomic DNA is extracted according to an ordinary method as described in Wataru Watanabe (comp.), Masahiro Sugiura (ed.), *Cloning and Sequence* (*Manual on Plant Biotechnology Experiments*), Tokyo, Noson Bunka-sha, 1989. The genomic DNA obtained is digested with appropriate restriction enzymes, and the resulting DNA fragments are fractionated by a known method such as sucrose density gradient centrifugation or sodium chloride density gradient centrifugation. For these fractionated DNA fragments, ordinary southern blot hybridization using the cDNA of the protein of the present invention as a probe (genomic southern method) is performed to determine the gene region coding for the desired information.

Further, this gene region is ligated to an appropriate vector such as a commercially available plasmid, phage or cosmid to produce a genomic DNA library. For this library, an ordinary screening by hybridization using the cDNA of the protein of the present invention as a probe is performed to obtain a genomic DNA clone containing a coding region for the amino acid sequence of the protein of the present invention. The genomic DNA clone obtained is subcloned into an appropriate vector favorable for the analysis of a gene sequence, such as a plasmid, and then subjected to the analysis of a base sequence according to an ordinary method, which makes it possible to determine the genomic DNA base sequence containing a coding region for the amino acid sequence of the protein of the present invention. Further, the transcription-initiating site of the genomic DNA of the protein of the present invention can be determined by the primer extension method as described in M. Bina-Stem et al., *Proc. Natl. Acad. Sci. USA*, 76, 731 (1979) or Sollner-Webb & R. H. Reeder, *Cell*, 18, 485 (1979), or the S1 mapping method as described in A. J. Berk & P. A. Sharp, *Proc. Natl. Acad. Sci. USA*, 75, 1274 (1978). One TATA sequence necessary for the initiation of transcription is present upstream the transcription-initiating site thus determined. In usual cases, a promotor sequence bearing the control of gene expression is present about 1 kb to about 10 kb upstream this transcription-initiating site. The promotor site of the gene of the present invention can be determined by utilizing the fact that the promotor of the gene of the present invention specifically acts in the roots. For example, gene fragments having promotor regions of different lengths are independently ligated to a reporter gene such as GUS, which is then introduced into a certain plant to produce a transgenic plant, and various tissues of the transgenic plant produced are examined for the expression of the reporter gene, by which the promotor site of the gene of the present invention can be finally determined.

On the other hand, a terminator sequence is present in the genomic DNA region corresponding to the site downstream the poly-A sequence which is usually present downstream the poly-A addition signal (i.e., AATAAA and consensus sequence) which is present in the 3' non-transrational region downstream the termination codon, and it has an effective function for terminating transcription.

The present invention will be further illustrated by the following examples, which are not to be construed to limit the scope thereof.

EXAMPLE 1

Separation and detection of the protein of the present invention

To 5 g of the root tissue of a commercially available carrot (variety name: Kuroda Gosun) was added 12.5 ml of a buffer for soluble-protein extraction (0.1M potassium phosphate (pH 8.0), 1 mM EDTA, 0.1% ascorbic acid, 0.25% 2-mercaptoethanol), and the mixture was ground in an ice bath with a whirling blender (Nihon Seiki) at 2000 rpm for 5 minutes. The ground material was filtered using 4 sheets of gauze, and the filtrate was centrifuged at 10,000 rpm at 4° C. for 10 minutes to obtain a supernatant. The supernatant was concentrated to a concentration of about 1 to 2 mg protein/ ml by a filter-filtration apparatus (Centriprep-10 (Amicon) and ultra-free CL unit (Millipore)). The concentrate was used as a sample and SDS-polyacrylamide gel electrophoresis was performed on an SDS-polyacrylamide gel with a 10–20% concentration ingredient of acrylamide, "SDS-PAG plate 10/20" (Daiichi Kagaku), in 0.0625M Tris-HCl (pH 6.8), 2% SDS, 10% glycerol, 5% 2-mercaptoethanol, 0.001% bromophenol blue, 1 liter buffer for electrophoresis (0.02M Tris, 0.192M glycine, 0.1% SDS, pH 8.4) at a constant current of 60 mA for 60 minutes to separate various proteins on the basis of their molecular weights. The separated proteins were silver-stained using a commercially available kit for silver staining, 2D-silver staining reagent II "Daiichi" (Daiichi Kagaku), and the pattern of protein separation was observed. The results are shown in FIG. 1. The protein of the present invention was detected at a position corresponding to a molecular weight of approximately 16 kD, and the ratio of its presence was about 10%, based on the total amount of proteins extracted from the root tissue, as determined by visual observation.

EXAMPLE 2

Determination of the N-terminal amino acid sequence of the protein of the present invention The concentrate of soluble proteins from the carrot root obtained in Example 1 was separated by the same electrophoresis as described in Example 1, and the separated proteins were stained according to a method as described in P. Matsudaria, *The Journal of Biological Chemistry* (1987). That is, the proteins in the gel were blotted on a commercially available polyvinylidene difluoride (PVDF) membrane in a blotting buffer (10 mM CAPS (3-cyclohexylaminopropane sulfonic acid)-10% methanol (pH 11.0)) at 100 V for 1 hour, stained by 0.1% Coomassie Brilliant Blue (CBB) R250/50% methanol, decolored in 50% methanol-10% acetic acid, and separated. The band including the protein of the present invention on the PVDF membrane stained by the CBB reagent was cut out by means of a cutter, and the protein of the present invention was collected. Then, 300 pmole of the collected protein of the present invention was analyzed for the amino acid sequence using the amino acid sequencer 473A (Applied Biosynthesis) according to the Edman degradation.

The results are shown in FIG. 2. The sequence consisting of 35 amino acids present at the N-terminus of the protein of the present invention was determined.

EXAMPLE 3

Preparation of carrot root cDNA library

In 10 ml of liquid nitrogen was frozen 10 g by fresh weight of the root tissue (9 weeks after seeding) of a commercially available carrot (variety name: Kuroda Gosun), and the frozen tissue was roughly ground by means of a mallet, and then thoroughly ground with a whirling blender (Nihon Seiki) at 1500 rpm for 25 minutes, while liquid nitrogen was added in several milliliters portions, to give fine powder. After vaporization of the liquid nitrogen, RNA extraction was performed using a commercially available RNA extraction kit (Extract-A-PLANT™ RNA ISOLATION KIT (Clontech)), and the entire RNA was collected from the extract by ethanol precipitation to give 520 µg of the entire RNA. The entire RNA was fractionated in a commercially available oligo-dT column (5'→3') to give 4.8 µg of poly-A RNA. From 1 µg of the poly-A tailed RNA, cDNA synthesis was performed using a commercially available cDNA synthesis kit (cDNA Synthesis System Plus, Amersham)to give 63 ng of cDNA. The cDNA was ligated to an EcoR I-Not I-BamH I adaptor (Takara Shuzo) using commercially available T4 ligase (Takara Shuzo), and a cDNA library composed of X phage in the XL1-BLUE strain derived from the *Escherichia coli* K-12 strain using EcoR I digested λ ZAPII (Stratagene) and a commercially available in vitro packaging kit (GIGA PACK II Gold (Stratagene)).

EXAMPLE 4

Screening of cDNA clones of the protein of the present invention

Based on the N-terminal amino acid sequence of the protein of the present invention as determined in Example 2, there were synthesized two kinds of synthetic probe DNAs each having the following presumed DNA base sequence:

(1) Probe 1:

5'-GGT GCC CAG AGC CAT GTI CTC GAG ATC ACT TCT TCA GTC TCC GCA GAG AAA ATA TTC AGC GGC ATT GTC CTT GAT GTT GAT ACA GTT ATT CCC AAG GCT GCC CCC-3', SEQ. I.D. NO.: 4

(2) Probe 2 (mixed probe):

5'-GGGGCG CAG AGG CAC GTG CTC GAG ATC-3', SEQ. I.D. NO.: 5, and
5'-GGGGCG CAA AGG CAC GTG CTC GAG ATC-3', SEQ. I.D. NO.: 6, wherein the symbol "I" in the sequence of probe 1 refers to inosine and probe 2 is a mixture of the above-identified synthetic DNAs. These synthetic probe DNAs were radiolabelled using a commercially available radiolabelling kit (MAGALABEL, Takara Shuzo) to give radiolabelled synthetic probe DNAs.

To *Escherichia coli* XLI-BLUE as a host was added $5.0 \times 10^4$ pfu of phage cDNA library, and the mixture was incubated at 37° C. for 15 minutes and then plated on an NZY plate of φ150 mm(1% NZ amine, 0.5% yeast extract, 0.5% NaCl, 1.5% agar), which was then incubated at 37° C. for 7 hours. The plate was cooled to 4° C. for 2 hours, and the plaque was transferred on commercially available nylon filters, Hybord-N (Amersham). After air-drying, these filters were denatured successively with an alkali denaturation solution (0.5M NaOH, 1.5M NaCl) for 2 minutes, a neutralization solution (0.5M Tris-HCl, pH 8.0, 1.5M NaCl) for 2 minutes, and 3×SSC (0.45M NaCl, 0.105M sodium citrate) for 2 minutes, and air-dried, followed by UV-light irradiation for DNA fixation on the filters. In a polyethylene bag were placed ten pieces of the filters, to which 25 ml of prehybridization buffer (6×SSC (0.9M NaCl, 0.21M sodium citrate), 5×Denhardt's solution (0.1% Ficoll 400, 0.1% polyvinylpyrrolidone, 0.1% BSA), 0.1% SDS, 100 µg/ml denatured salmon sperm DNA) was added, and the contents of the bag were incubated at 45° C. for 2 hours. Then, the prehybridization buffer was removed, and 6 ml of fresh prehybridization buffer was added. Further, $10^7$ cpm of the RI-labelled synthetic probe DNA obtained by the above method was added, and the mixture was incubated at 45° C. overnight. The filters were removed and then washed by successive incubation in 50 ml of 6×SCC at room temperature for 5 minutes; in 100 ml of 6×SSC at room temperature for 5 minutes; and in 100 ml of 6 ×SSC-10% SDS at 45° C. for 5 minutes, after which a plaque containing the cDNA for the protein of the present invention was obtained by the RI activity on the filters. The signal plaque obtained was isolated in a solution containing 500 µl of SM (50 mM Tris-HCl, pH 7.5, 0.1M NaCl, 7 mM $MgSO_4$, 0.01% gelatin) and 20 µl of chloroform. Further, to obtain a single clone, *Escherichia coli* XLI-BLUE and $10^3$-$10^2$ pfu of phage solution were mixed, and the mixture was incubated at 37° C. for 15 minutes and plated on an NZY plate of φ90 mm, which was then incubated at 37° C. overnight. This plate was transferred to nylon membranes by the above method, and two cDNA clones for the protein of the present invention were isolated by plaque hybridization using the same synthetic probe DNA as described above.

EXAMPLE 5

Figure 3:
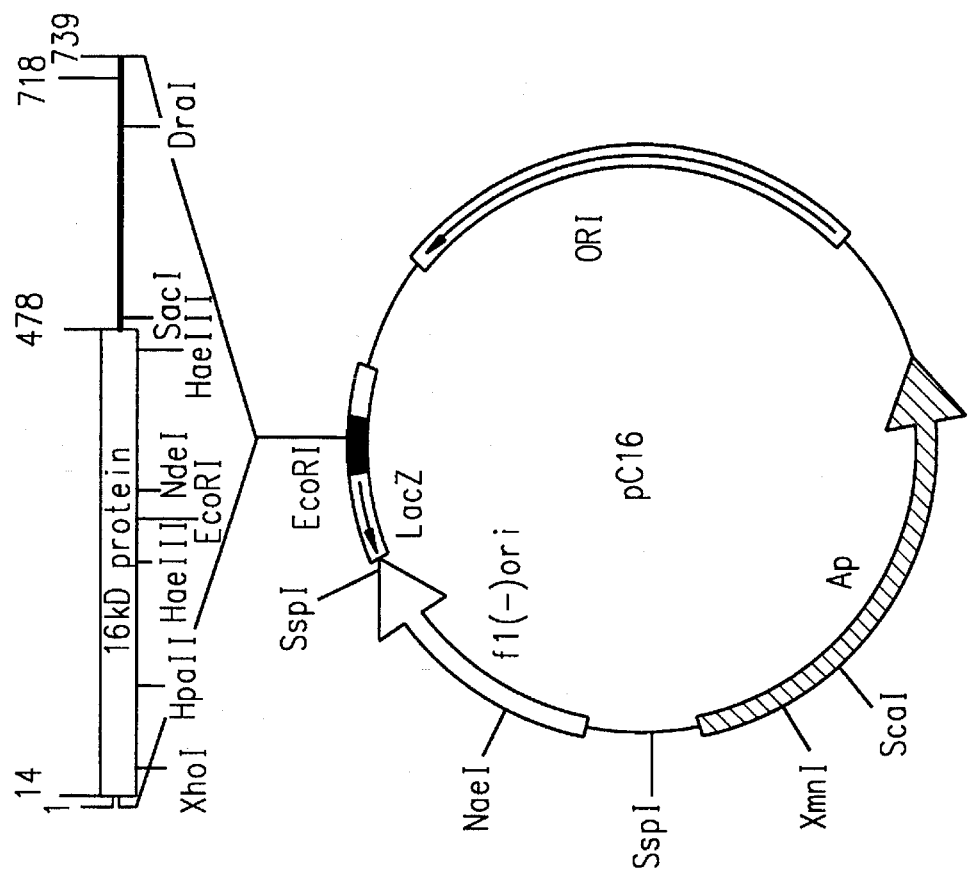
FIG. 3 shows the structure of plasmid pC 16 containing the gene coding for the protein of the present invention.

Analysis of insert in cDNA clones for the protein of the present invention; and determination of the base sequence coding for the protein of the present invention and the corresponding amino acid sequence The two cDNA clones obtained in Example 4 were subcloned into plasmid vector pBluescript SK(−) by an ordinary method as described in J. Sambrook, E. F. Fritsch & T. Maniatis, *Molecular Cloning Second Edition*, Cold Spring Harbor Laboratory Press (1989) to give plasmid cDNA clones, pC16-1 and pC16-2. The base sequence of the inserts in these cDNA clones was determined by DNA Sequencer 373A (Applied Biosystems) using Taq Dye Primer Cycle Sequencing Kit and Taq Dye Deoxy Terminator Cycle Sequencing Kit (Applied Biosystems). The pC16-1 and pC16-2 both have an insert having the same base sequence. For this reason, these plasmids were identical and designated pC16 (see FIG. 3). The pC16 has been deposited as *Escherichia coli* XL1-BLUE/pC16 (accession number: FERM BP-4469) with the National Institute of Bioscience and Human-Technology, Agency of Industrial Science and Technology under the Budapest treaty (date of the original deposit: Nov. 17, 1993). The insert had a size of 739 bases (see Sequence Listing, SEQ ID NO: 3), in which 465 bases at the 14th to the 478th positions were found to constitute a coding region for the 16 kD protein which can be specifically expressed in carrot roots. It was also found that bases at the 479th to the 717th positions constitute a 3' non-transrational region and twenty-two pieces of adenine at the 718th to the 739th positions constitute a poly-A tail. From the base sequence of the coding region for the 16 kD protein which can be specifically expressed in carrot roots, the entire amino acid sequence of the protein was determined (see Sequence Listing, SEQ ID NO: 2). The protein of the present invention comprises 154 amino acids (see Sequence Listing, SEQ ID NO: 1), and it has a calculated molecular weight of 16125.02.

EXAMPLE 6

Tissue-specific expression of the protein of the present invention

The seeds of a commercially available carrot (variety name: Kuroda Gosun) were sowed in the soil of a pot in a greenhouse, and cultivated. On the 4th, 7th, 9th and 21st weeks after the sowing, the plants were collected and separated into the root (subterranean) tissue and the leaf (terrestrial) tissue. All the proteins in the respective tissues were extracted and concentrated by the same method as described in Example 1, and SDS-polyacrylamide gel electrophoresis was performed with 1 μg of the protein per lane as a sample under the same conditions as described in Example 1, by which various proteins were separated on the basis of their molecular weights and compared for the expression of the protein of the present invention.

Figure 4:
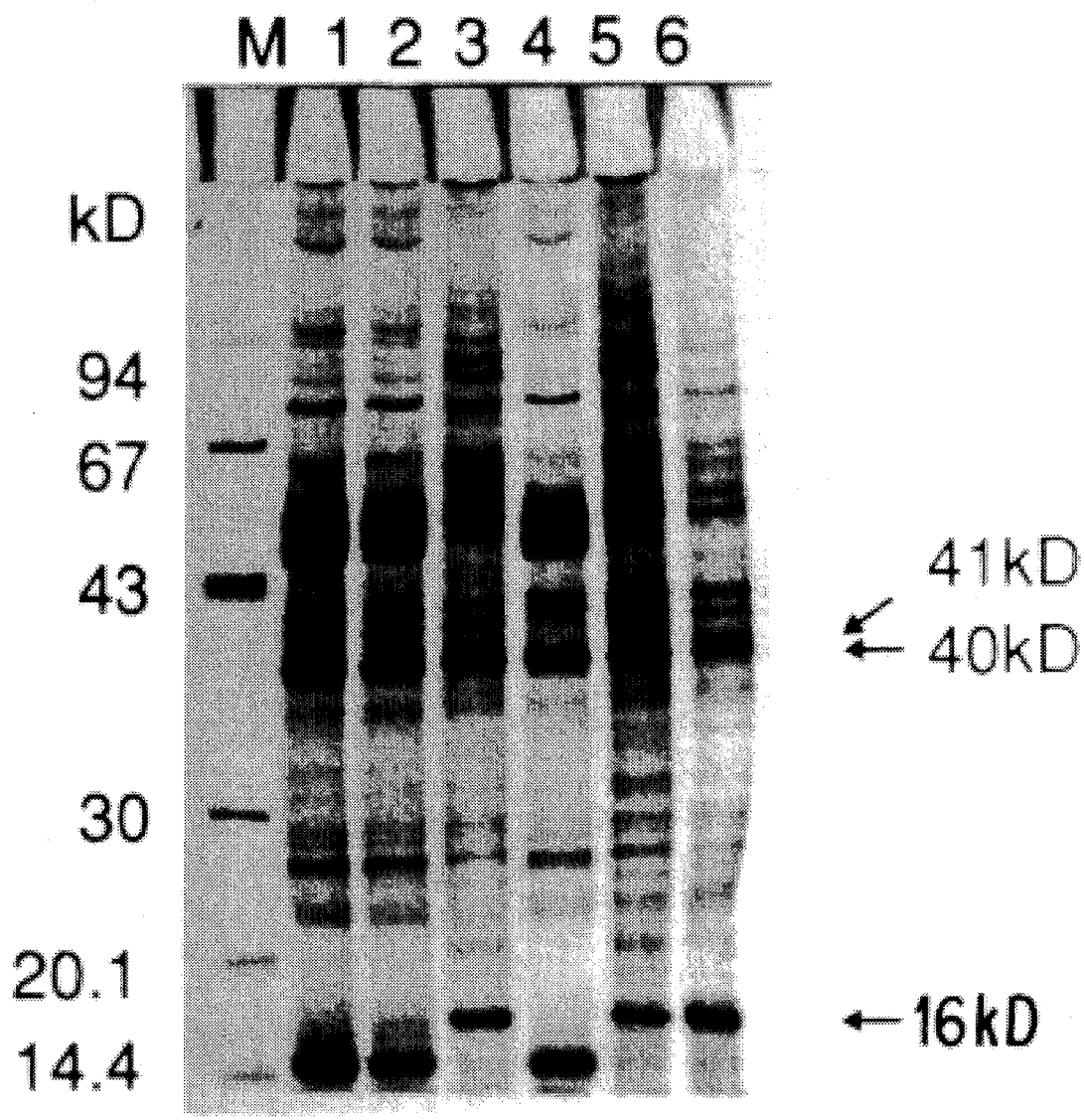
FIG. 4 shows the results of the SDS-polyacrylamide electrophoresis (with silver staining) which was performed to examine the tissue specificity of the protein of the present invention. Lane M is corresponding to a molecular weight marker; lane 1, the sample of all the proteins present in the entire plant on the 4th week after the seeding; lane 2, the sample of all the proteins present in the leaves on the 7th week after the seeding; lane 3, the sample of all the proteins present in the roots on the 7th week after the seeding; lane 4, the sample of all the proteins present in the leaves on the 9th week after the seeding; lane 5, the sample of all the proteins present in the roots on the 9th week after the seeding; and lane 6, the sample of all the proteins on the 21st week after the seeding. The arrow indicates the band corresponding to the protein of the present invention.

The results are shown in FIG. 4. All the proteins in the entire plant on the 4th week was compared with those in the root and leaf at the 7th, 9th and 21st weeks, respectively, and it is found that the expression of the protein of the present invention is notably different. That is, the protein of the present invention was not expressed in the young plants or in the respective leaf tissues, but expressed only in the root tissues; it is further clear that the protein of the present invention is a reserve protein having an increased ratio to all the proteins with a progress of the growth of the root tissues.

EXAMPLE 7

Comparison between the varieties of the protein of the present invention

From the root tissues of various commercially available carrots (variety names: Kuroda Gosun, Early Chantenee, Imperator and Nuntesscarlet), all the proteins were extracted and concentrated by the same method as described in Example 1, and SDS-polyacrylamide electrophoresis was performed with 1 μg of the protein per lane as a sample under the same conditions as described in Example 1, by which various proteins were separated on the basis of their molecular weights and compared for the expression of the protein of the present invention.

Figure 5:
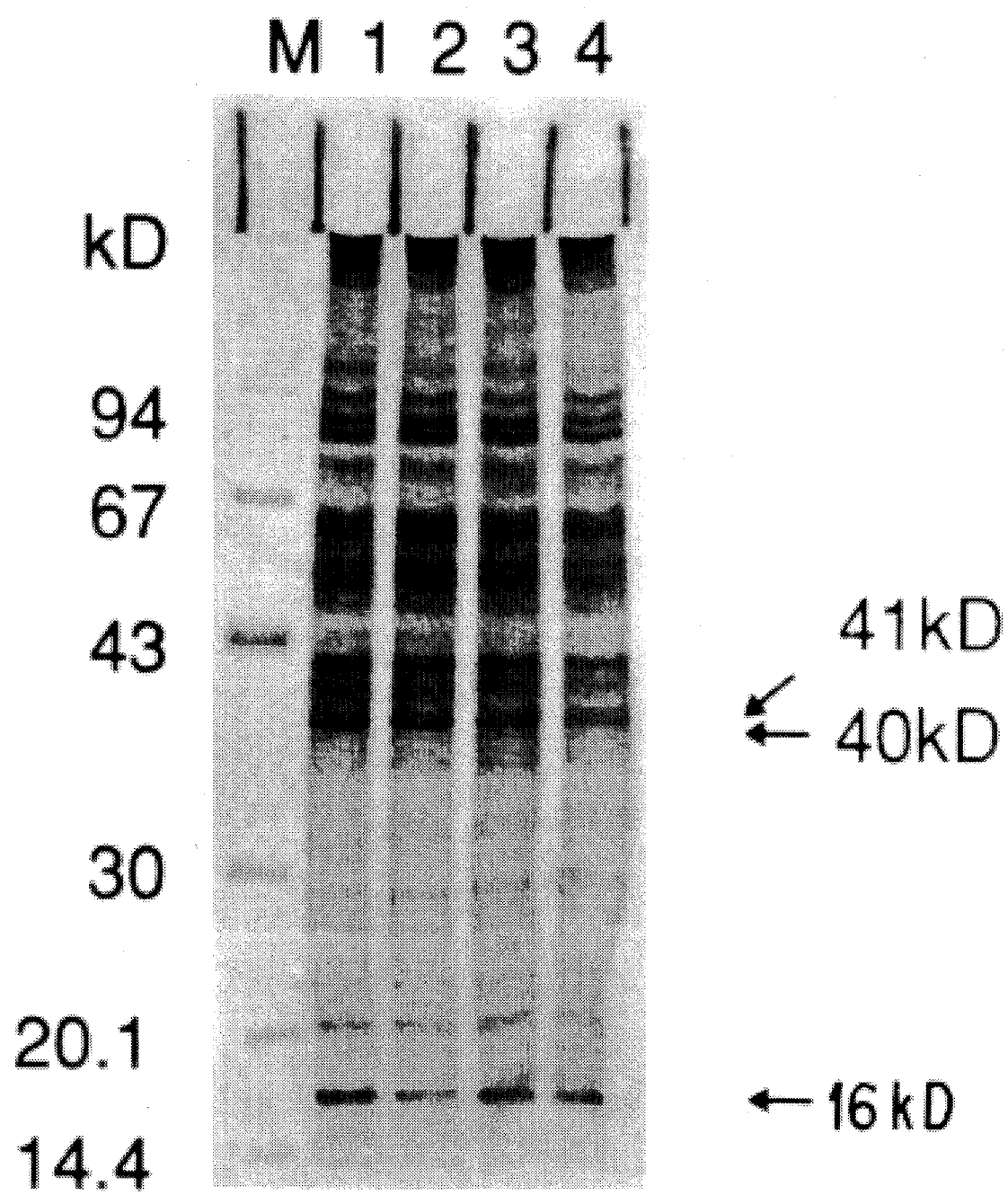
FIG. 5 shows the results of the SDS-polyacrylamide electrophoresis (with silver staining) which was performed to examine the comparison between the varieties of the protein of the present invention. Lane M is corresponding to a molecular weight marker; lane 1, the sample of all the protein present in the root of carrot "Kuroda Gosun"; lane 2, the sample of all the proteins present in the root of carrot "Early-chantenee"; lane 3, the sample of all the proteins present in the root of carrot "Imperator"; and lane 4, the sample of all the proteins present in the root of carrot "Nuntesscarlet". The arrow indicates the band corresponding to the protein of the present invention.

The results are shown in FIG. 5. It was found that the protein of the present invention is the most important protein corresponding to about 10% of all the proteins, regardless of the kind of variety.

EXAMPLE 8

Homology of the protein of the present invention

Genes and amino acid sequences, which have high homology with the base sequence coding for the protein of the present invention and the corresponding amino acid sequence, respectively, as determined in Example 5, were searched on the data bases EMBL and NBRF. As a result, it was found that the gene and amino acid sequence of the present invention exhibit the highest homology with the genes and amino acid sequences of several proteins related to plant disease resistance (see FIG. 6). The proteins having the highest homology were Pathogenesis-related Protein (PR-Protein) 1-3, 1-1 and 1-2 of parsley belonging to the family *Umbelliferae* similarly to carrot (see FIG. 6). Relatively high homology was also observed in the mRNA of 3T3-7, 3T3-9 and 3T3-M1 clones of HSP60 which is a heat shock protein of mice.

As described above, the gene and plasmid of the present invention are useful for higher expression of the protein of the present invention, which is specifically present in carrot roots, and it becomes possible to develop high protein carrots by such higher expression.

What is claimed is:

1. A protein corresponding to a molecular weight of approximately 16 kD and having the amino acid sequence as shown in Sequence Listing, SEQ ID NO: 1.

2. A gene containing a coding region for the amino acid sequence of the protein according to claim 1.

3. A gene coding for a protein corresponding to a molecular weight of approximately 16 kD, said gene having the base sequence as shown in Sequence Listing, SEQ ID NO: 2.

4. A plasmid containing the gene according to claim 2.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 154 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO (vi) ORIGINAL SOURCE:
    (A) ORGANISM: Daucus carota
    (B) STRAIN: Kuroda Gosun (xi) SEQUENCE DESCRIPTION: SEQ ID NO:1:

```
Met Gly Ala Gln Ser His Ser Leu Glu Ile Thr Ser Ser Val Ser Ala
 1               5                  10                 15
Glu Lys Ile Phe Ser Gly Ile Val Leu Asp Val Asp Thr Val Ile Pro
            20                 25                 30
Lys Ala Ala Pro Gly Ala Tyr Lys Ser Val Asp Val Lys Gly Asp Gly
        35                 40                 45
Gly Ala Gly Thr Val Arg Ile Ile Thr Leu Pro Glu Gly Ser Pro Ile
    50                 55                 60
Thr Ser Met Thr Val Arg Thr Asp Ala Val Asn Lys Glu Ala Leu Thr
65                  70                 75                  80
Tyr Asp Ser Thr Val Ile Asp Gly Asp Ile Leu Leu Glu Phe Ile Glu
                85                 90                 95
Ser Ile Glu Thr His Met Val Val Val Pro Thr Ala Asp Gly Gly Ser
               100                105                110
Ile Thr Lys Thr Thr Ala Ile Phe His Thr Lys Gly Asp Ala Val Val
           115                120                125
Pro Glu Glu Asn Ile Lys Phe Ala Asp Ala Gln Asn Thr Ala Leu Phe
       130                135                140
Lys Ala Ile Glu Ala Tyr Leu Ile Ala Asn
145                150
```

(2) INFORMATION FOR SEQ ID NO:2:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Daucus carota
        (B) STRAIN: Kuroda Gosun (xi) SEQUENCE DESCRIPTION: SEQ ID NO:2:

```
ATGGGTGCCC AGAGCCATTC ACTCGAGATC ACTTCTTCAG TCTCCGCAGA GAAAATATTC    60
AGCGGCATTG TCCTTGATGT TGATACAGTT ATTCCCAAGG CTGCCCCCGG AGCTTACAAG   120
AGTGTCGATG TTAAAGGAGA CGGTGGAGCT GGAACCGTCA GAATTATCAC CCTTCCCGAA   180
GGTAGCCCAA TCACCTCAAT GACGGTTAGG ACTGATGCAG TGAACAAGGA GGCCTTGACA   240
TACGATTCCA CAGTCATTGA TGGAGACATC CTTCTAGAAT TCATCGAATC CATTGAAACC   300
CATATGGTAG TTGTGCCAAC TGCTGACGGA GGTAGCATTA CCAAGACCAC TGCCATATTC   360
CACACCAAAG GCGATGCCGT GGTTCCTGAG GAGAACATCA AGTTTGCAGA TGCTCAGAAC   420
ACTGCTCTTT TCAAGGCTAT TGAGGCCTAC CTCATTGCTA ATTAA                  465
```

(2) INFORMATION FOR SEQ ID NO:3:

(i) SEQUENCE CHARACTERISTICS:
        (A) LENGTH: 739 base pairs
        (B) TYPE: nucleic acid 5,512,484

13

14

-continued ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Daucus carota
        ( B ) STRAIN: Kuroda Gosun ( x i ) SEQUENCE DESCRIPTION: SEQ ID NO:3:

| | | | | | | |
|---|---|---|---|---|---|---|
| CATTCTAAAT | ATCATGGGTG | CCCAGAGCCA | TTCACTCGAG | ATCACTTCTT | CAGTCTCCGC | 60 |
| AGAGAAAATA | TTCAGCGGCA | TTGTCCTTGA | TGTTGATACA | GTTATTCCCA | AGGCTGCCCC | 120 |
| CGGAGCTTAC | AAGAGTGTCG | ATGTTAAAGG | AGACGGTGGA | GCTGGAACCG | TCAGAATTAT | 180 |
| CACCCTTCCC | GAAGGTAGCC | CAATCACCTC | AATGACGGTT | AGGACTGATG | CAGTGAACAA | 240 |
| GGAGGCCTTG | ACATACGATT | CCACAGTCAT | TGATGGAGAC | ATCCTTCTAG | AATTCATCGA | 300 |
| ATCCATTGAA | ACCCATATGG | TAGTTGTGCC | AACTGCTGAC | GGAGGTAGCA | TTACCAAGAC | 360 |
| CACTGCCATA | TTCCACACCA | AAGGCGATGC | CGTGGTTCCT | GAGGAGAACA | TCAAGTTTGC | 420 |
| AGATGCTCAG | AACACTGCTC | TTTTCAAGGC | TATTGAGGCC | TACCTCATTG | CTAATTAAGC | 480 |
| TGAGCTCTCA | ACTTCCGTAA | TTTTATGAGT | GAGTGGAGGA | ATTGCAACGT | TTTCTTTTGT | 540 |
| GTTTTGTTTT | CGAGCAACTT | CATAATTTAC | AGAGTGAGTG | ACAGTCAGTG | ACAGAATTGC | 600 |
| AACTTTCTCT | TTGTACTTTG | TTGTGACTTG | TGATGAATAA | CTTCATCTGG | CTGGTAATGT | 660 |
| ATGCGATCTT | TTTAAATAAT | ATGCACTATT | ATTAAACCAA | TAATCATATT | CATTCTCAAA | 720 |
| AAAAAAAAA | AAAAAAAA | | | | | 739 |

( 2 ) INFORMATION FOR SEQ ID NO:4:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Synthetic DNA probe"

( i i i ) HYPOTHETICAL: NO ( i v ) ANTI-SENSE: NO ( i x ) FEATURE:
        ( A ) NAME/KEY: misc_feature
        ( B ) LOCATION: 17..19
        ( D ) OTHER INFORMATION: /note="N =Inosine"

( x i ) SEQUENCE DESCRIPTION: SEQ ID NO:4:

| | | | | | | |
|---|---|---|---|---|---|---|
| GGTGCCCAGA | GCCATGTNCT | CGAGATCACT | TCTTCAGTCT | CCGCAGAGAA | AATATTCAGC | 60 |
| GGCATTGTC | CTTGATGTTG | ATACAGTTAT | TCCCAAGGCT | GCCCC | | 105 |

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Synthetic DNA probe"

( i i i ) HYPOTHETICAL: NO ( i v ) ANTI-SENSE: NO ( x i ) SEQUENCE DESCRIPTION: SEQ ID NO:5:

GGGGCGCAGA GGCACGTGCT CGAGATC                                                                    2 7

( 2 ) INFORMATION FOR SEQ ID NO:6:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc ="Synthetic DNA probe"

( i i i ) HYPOTHETICAL: NO ( i v ) ANTI-SENSE: NO ( x i ) SEQUENCE DESCRIPTION: SEQ ID NO:6:

GGGGCGCAAA GGCACGTGCT CGAGATC                                                                    2 7